US012566148B2

(12) United States Patent
Shelton et al.

(10) Patent No.: US 12,566,148 B2
(45) Date of Patent: Mar. 3, 2026

(54) HYDROGEN SULFIDE SENSOR AND ASSOCIATED METHODS

(71) Applicant: LUTUM TECHNOLOGY, LLC, Hanover, NH (US)

(72) Inventors: Katherine Shelton, Lebanon, NH (US); Joseph J. BelBruno, Hanover, NH (US)

(73) Assignee: LUTUM TECHNOLOGY, LLC, Hanover, NH (US)

( * ) Notice: Subject to any disclaimer, the term of this patent is extended or adjusted under 35 U.S.C. 154(b) by 65 days.

(21) Appl. No.: 17/551,978

(22) Filed: Dec. 15, 2021

(65) Prior Publication Data

US 2022/0187231 A1     Jun. 16, 2022

Related U.S. Application Data

(60) Provisional application No. 63/126,478, filed on Dec. 16, 2020.

(51) Int. Cl.
     *G01N 27/12*      (2006.01)
     *G01N 33/00*      (2006.01)
(52) U.S. Cl.
     CPC ....... *G01N 27/125* (2013.01); *G01N 33/0044* (2013.01)
(58) Field of Classification Search
     CPC .......................... G01N 27/125; G01N 33/0044
     See application file for complete search history.

(56) References Cited

U.S. PATENT DOCUMENTS

| | | | |
|---|---|---|---|
| 9,932,449 B2 | 4/2018 | Serban et al. | |
| 2002/0131901 A1* | 9/2002 | Monkman ............ | G01N 27/126 |
| | | | 436/118 |
| 2010/0005858 A1* | 1/2010 | Virji ..................... | G01N 27/127 |
| | | | 73/31.05 |
| 2013/0040397 A1* | 2/2013 | Star ..................... | G01N 33/0044 |
| | | | 977/788 |

(Continued)

OTHER PUBLICATIONS

Arabi, Mohamed, et al. "Detection of volatile organic compounds by using MEMS sensors." Sensors 22.11 (2022): 4102. (Year: 2022).*

(Continued)

*Primary Examiner* — Fatemeh Esfandiari Nia
(74) *Attorney, Agent, or Firm* — Cozen O'Connor

(57) ABSTRACT

A hydrogen sulfide sensor includes a substrate, a par of interdigitated electrodes disposed on the substrate, and a homogeneous polyaniline sensing film disposed on the pair of interdigitated electrodes and having electrical conductivity that depends upon a concentration of hydrogen sulfide. A method for detecting hydrogen sulfide includes for each sensor of a plurality of sensors: generating a signal if said sensor is exposed to a sample of hydrogen sulfide having density greater than or equal to a hydrogen sulfide detection threshold of said sensor, wherein the plurality of sensors has a respective plurality of hydrogen sulfide detection limits that span a detection range. A method for forming a hydrogen sulfide sensor includes dissolving a polyaniline polymer and a metal-chloride salt in an organic solvent to form a solution, and spin-coating the solution to form a homogeneous sensing film disposed on a pair of interdigitated electrodes disposed on a substrate.

12 Claims, 4 Drawing Sheets

(56) References Cited

U.S. PATENT DOCUMENTS

| | | | |
|---|---|---|---|
| 2014/0197046 A1* | 7/2014 | Busnaina | G01N 27/4146 |
| | | | 205/786.5 |
| 2014/0227795 A1* | 8/2014 | Belbruno | G01N 33/0047 |
| | | | 427/596 |
| 2016/0011142 A1* | 1/2016 | Serban | C08J 3/21 |
| | | | 427/565 |
| 2020/0232970 A1* | 7/2020 | Haick | G01L 19/0092 |
| 2020/0377648 A1* | 12/2020 | Ngai | C08G 61/124 |

OTHER PUBLICATIONS

Virji, Shabnam, et al. "Polyaniline nanofiber composites with metal salts: chemical sensors for hydrogen sulfide." Small 1.6 (2005): 624-627 (Year: 2005).*

Crowley, K. et al., "Fabrication of Polyaniline-Based Gas Sensors Using Piezoelectric Inkjet and Screen Printing for the Detection of Hydrogen Sulfide", IEEE Sensors Journal, 10(9): 1419-1426 (2010).

Li, D. et al., "Ultra-highly sensitive and selective $H_2S$ gas sensor based on CuO with sub-ppb detection limit", International Journal of Hydrogen Energy, 44: 3985-3992 (2019).

Pandey, S., "Highly sensitive and selective chemiresistor gas/vapor sensors based on polyaniline nancomposite: A comprehensive review", Journal of Science: Advanced Materials and Devices, 1: 431-453 (2016).

Sarfraz, J. et al., "Low-Cost Hydrogen Sulfide Gas Sensor on Paper Substrates: Fabrication and Demonstration", IEEE Sensors Journal, 12(6): 1973-1978 (2012).

Sarfraz, J. et al., "Printed hydrogen sulfide gas sensor on paper substrate based on polyaniline composite", Thin Solid Films, 534: 621-628 (2013).

* cited by examiner

100

110

C 198X
198Z
198Y

130

120(1)

120(2)

B

B

C

C

120(1)  110  120(2)  132

130

198Z
198Y
198X

C

B  110  120(2)  132

130

120(1)

198Z
198X
198Y

B

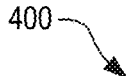

400

410
FOR EACH SENSOR OF A PLURALITY OF SENSORS, GENERATE A SIGNAL IF SAID SENSOR IS EXPOSED TO A SAMPLE OF HYDROGEN SULFIDE HAVING GAS DENSITY GREATER THAN OR EQUAL TO A HYDROGEN SULFIDE DETECTION THRESHOLD OF SAID SENSOR.

*FIG. 4*

500

510
DEPOSIT A PAIR OF ELECTRODES ON A SUBSTRATE.

520
DISSOLVE A POLYANILINE POLYMER AND A METAL-CHLORIDE SALT IN AN ORGANIC SOLVENT TO FORM A SOLUTION.

530
SPIN-COAT THE SOLUTION TO FORM A HOMOGENEOUS SENSING FILM DISPOSED ON THE PAIR OF ELECTRODES.

*FIG. 5*

HYDROGEN SULFIDE SENSOR AND ASSOCIATED METHODS

RELATED APPLICATION

This application claims priority to U.S. Provisional Patent Application No. 63/126,478, filed Dec. 16, 2020, the entirety of which is incorporated herein by reference.

BACKGROUND

Hydrogen sulfide is a colorless, flammable gas that can be toxic if inhaled. Hydrogen sulfide sensors are used in various industries. The United States Occupation Safety and Health Administration established worker exposure limits on the permissible amount of hydrogen sulfide, often measured in parts per million, ppm. The peak limit is 50 ppm (for up to 10 minutes) and the limit for an 8-hour shift is 10 ppm. However, hydrogen sulfide gas is harmful even a low concentrations. When one is exposed to hydrogen sulfide gas, it is essential to seek medical attention. Accordingly, in many industrial situations, it is important to be able to detect the gas in very low concentrations as soon as possible in the event a leak occurs.

SUMMARY OF THE INVENTION

Embodiments disclosed herein detect hydrogen sulfide. In a first aspect, a hydrogen sulfide sensor includes a substrate, a pair of interdigitated electrodes disposed on the substrate, and a homogeneous polyaniline sensing film disposed on the pair of interdigitated electrodes. The homogeneous polyaniline sensing film has electrical conductivity that depends upon a concentration of hydrogen sulfide.

In a second aspect, a hydrogen sulfide sensing system includes a plurality of sensors, each with a homogeneous polyaniline sensing film with electrical conductivity that depends on a concentration of hydrogen sulfide.

In a third aspect, a method for detecting hydrogen sulfide includes, for each sensor of a plurality of sensors, generating a signal if said sensor is exposed to a sample of hydrogen sulfide having gas density greater than or equal to a hydrogen sulfide detection threshold of said sensor. The plurality of sensors has a respective plurality of hydrogen sulfide detection limits that span a detection range.

In a fourth aspect, a method for forming a hydrogen sulfide sensor includes (i) dissolving a polyaniline polymer and a metal-chloride salt in an organic solvent to form a solution, and (ii) spin-coating the solution to form a homogeneous sensing film disposed on a pair of interdigitated electrodes disposed on a substrate.

BRIEF DESCRIPTION OF THE FIGURES

FIG. 4 is a flowchart illustrating a method for detecting hydrogen sulfide.

FIG. 5 is a flowchart illustrating a method for forming a hydrogen sulfide sensor.

DETAILED DESCRIPTION OF THE DRAWINGS

Figure 1A:
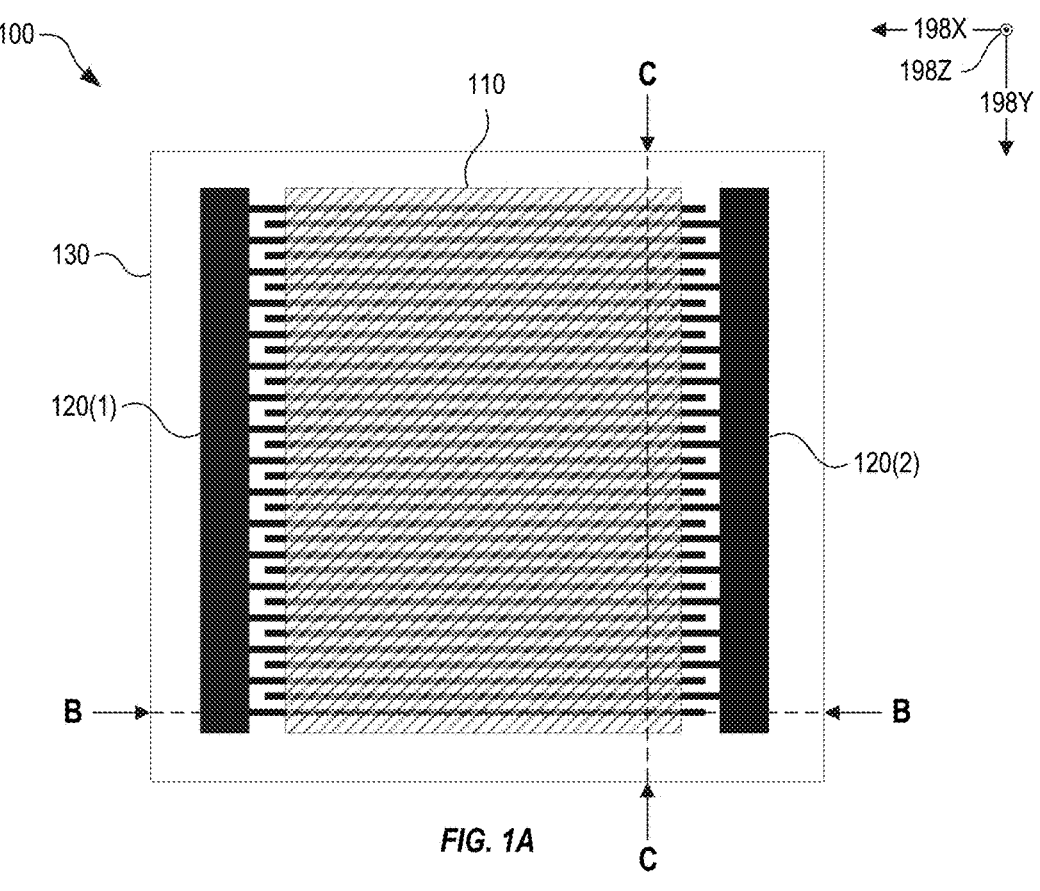
FIGS. 1A, 1B, and 1C, according to an embodiment.
Figure 1B:
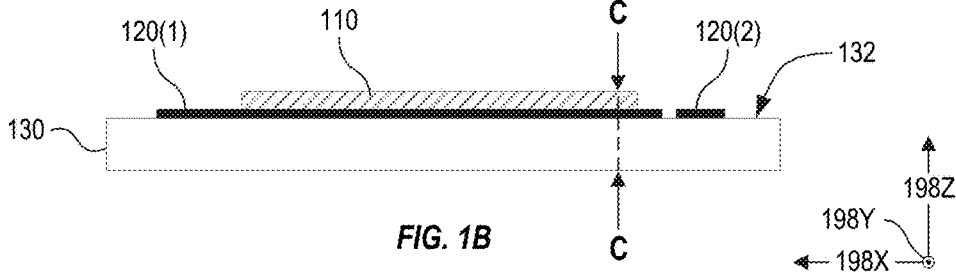
Figure 1C:
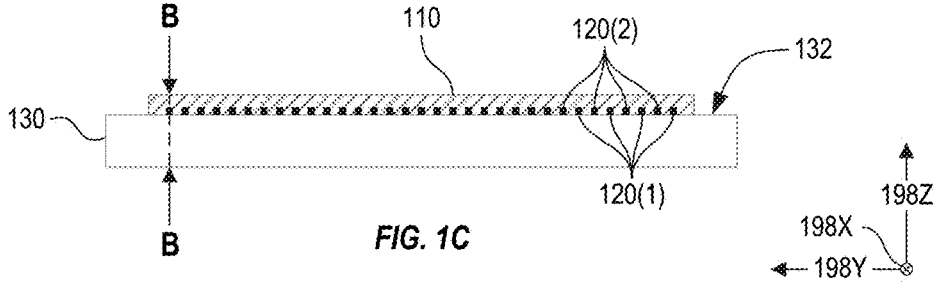

FIGS. 1A, 1B and 1C illustrate three views of a hydrogen sulfide sensor 100 with homogeneous polyaniline sensing film 110, according to an embodiment. FIGS. 1A, 1B, and 1C are best viewed together in the following description. The top view illustrated in FIG. 1A is parallel to a plane, hereinafter the x-y plane, formed by orthogonal axes 198X and 198Y, which are each orthogonal to an axis 198Z. The x-y plane and planes parallel to the x-y plane are referred to as horizontal planes. Unless otherwise specified, heights of objects herein refer to the object's extent along axis 198Z. Herein, a reference to an axis x, y, or z refers to axes 198X, 198Y, and 198Z respectively. Also, herein, a width refers to an object's extent along the x axis, a depth refers to an object's extent along the y axis, a thickness (or thinness) refers to an object's extent along the z axis, and vertical refers to a direction along the z axis. Also, herein, "above" refers to a relative position a distance away along the axis 198Z in the positive direction and "below" refers to a relative position a distance away along the axis 198Z in the negative direction. The section line B-B in FIG. 1A indicates the location of the orthogonal cross-sectional side view illustrated in FIG. 1B, which is parallel to x-z plane. The section line C-C in FIG. 1A indicates the location of the orthogonal cross-sectional side view illustrated in FIG. 1C, which is parallel to the y-z plane.

The hydrogen sulfide sensor 100 includes a pair of interdigitated electrodes 120 (120(1) and 120(2), individually), which are disposed on a substrate 130 that has a top surface 132. In the embodiment illustrated in FIGS. 1A, 1B and 1C, the homogeneous polyaniline sensing film 110 is formed by depositing a solution rather than by depositing a dispersion. Deposition of a solution leads to a homogeneous film while deposition of a dispersion leads to a patchy, inhomogeneous film. The homogeneous polyaniline sensing film 110 may for example be deposited using a spin-coating technique, though other solution-based deposition techniques may be used without departing from the scope hereof.

The homogeneous polyaniline sensing film 110 exhibits an electrical conductivity that increases when exposed to increasing concentration of hydrogen sulfide. Further, the electrical conductivity of the homogeneous polyaniline sensing film 110 decreases when exposed to decreasing concentration of hydrogen sulfide, thereby making the hydrogen sulfide sensor 100 "reversible". Reversible sensors provide a measurement of the present concentration of target gas, rather than irreversibly reaching a threshold. As a result, reversible sensors are reusable and continue to be usable after a large and repeated exposure to a target species, for example hydrogen sulfide. Other dependencies of the electrical conductivity on the hydrogen sulfide concentration are included within the scope hereof.

The homogeneous polyaniline sensing film 110 of FIGS. 1A, 1B, and 1C includes a metal-chloride salt. The electrical conductivity changes with respect to hydrogen sulfide concentration at a given rate, which can be described by the conductivity derivative of the homogeneous polyaniline sensing film 110. The concentration of the metal-chloride salt in the homogeneous polyaniline sensing film 110 may be selected to achieve a desired conductivity derivative. This conductivity derivative may be selected by altering the concentration of the metal-chloride salt, thereby making the sensitivity of the hydrogen sulfide sensor 100 adjustable.

The sensitivity of the hydrogen sulfide sensor 100 may be further adjusted by altering the identity of the metal-chloride salt. One or more of $CuCl_2$, $ZnCl_2$, and $FeCl_2$ is selected to achieve a desired conductivity derivative of the electrical conductivity with respect to concentration of hydrogen sulfide. The homogeneous polyaniline sensing film 110 of FIGS. 1A, 1B, and 1C further includes a polyaniline polymer. The sensitivity of the hydrogen sulfide sensor 100 may be adjusted by adjusting the concentration of polyaniline polymer in the homogenous polyaniline sensing film 110. Thus, the sensitivity of the hydrogen sulfide sensor 100 may be adjusted by one or more of (i) the metal-chloride concentration, (ii) the metal-chloride identity, and (iii) the concentration of the polyaniline polymer, all of which are selected to achieve a sensitivity to hydrogen sulfide with density between 1 ppb and 250 ppm.

The hydrogen sulfide sensor 100 includes the substrate 130, which in the embodiment illustrated in FIGS. 1A, 1B, and 1C is formed of glass. The pair of interdigitated electrodes 120 is for example formed of chromium. In other embodiments, the electrodes are formed by coating printed circuit board electrodes with one of gold and silver using, for example, a plotter coating system. The homogeneous polyaniline sensing film 110 has a thickness of one micron, though the thickness may be as small as one hundred nanometers.

Figure 2A:
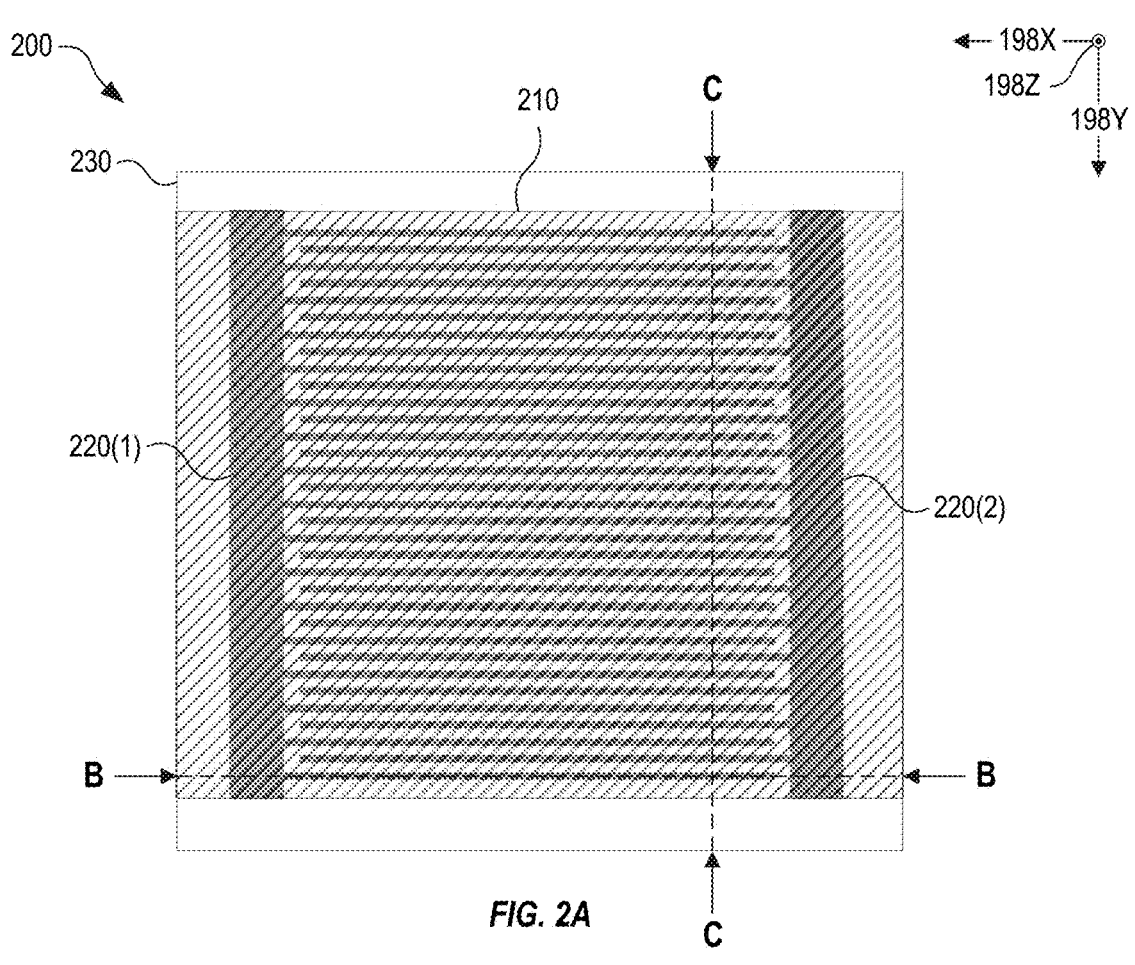
Figure 2B:
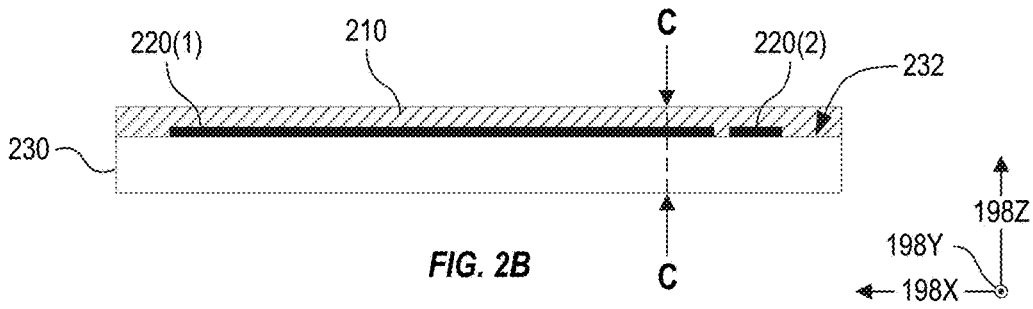
Figure 2C:
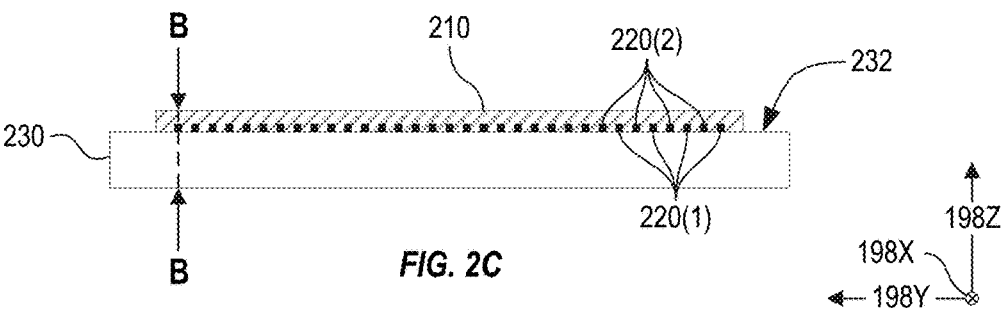

FIGS. 2A, 2B, and 2C illustrate three views of a hydrogen sulfide sensor 200 with full-width homogeneous polyaniline sensing film 210. The hydrogen sulfide sensor 200 is an example of the hydrogen sulfide sensor 100 of FIGS. 1A, 1B, and 1C. The section line B-B in FIG. 2A indicates the location of the orthogonal cross-sectional side view illustrated in FIG. 2B, which is parallel to x-z plane. The section line C-C in FIG. 2A indicates the location of the orthogonal cross-sectional side view illustrated in FIG. 2C, which is parallel to the y-z plane.

The hydrogen sulfide sensor 200 includes a pair of interdigitated electrodes 220 (220(1) and 220(2), individually), which are disposed on a substrate 230 that has a top surface 232. In the embodiment illustrated in FIGS. 2A, 2B, and 2C, the width of the homogeneous polyaniline sensing film 210 is equal to the width of the substrate 230. The homogeneous polyaniline sensing film 210 may have a smaller width, with respect to the substrate 230, without departing from the scope hereof. The depth (distance along the y-axis) of the homogeneous polyaniline sensing film 210 with respect to the depth of the substrate 230 may vary without departing from the scope hereof.

The hydrogen sulfide sensor 200, homogeneous polyaniline sensing film 210, pair of interdigitated electrodes 220, substrate 230, and top surface 232 are respective examples of the hydrogen sulfide sensor 100, homogeneous polyaniline sensing film 110, pair of interdigitated electrodes 120, substrate 130, and top surface 132 of FIGS. 1A, 1B, 1C and the descriptions of each respective elements apply between the two figures.

Figure 3:
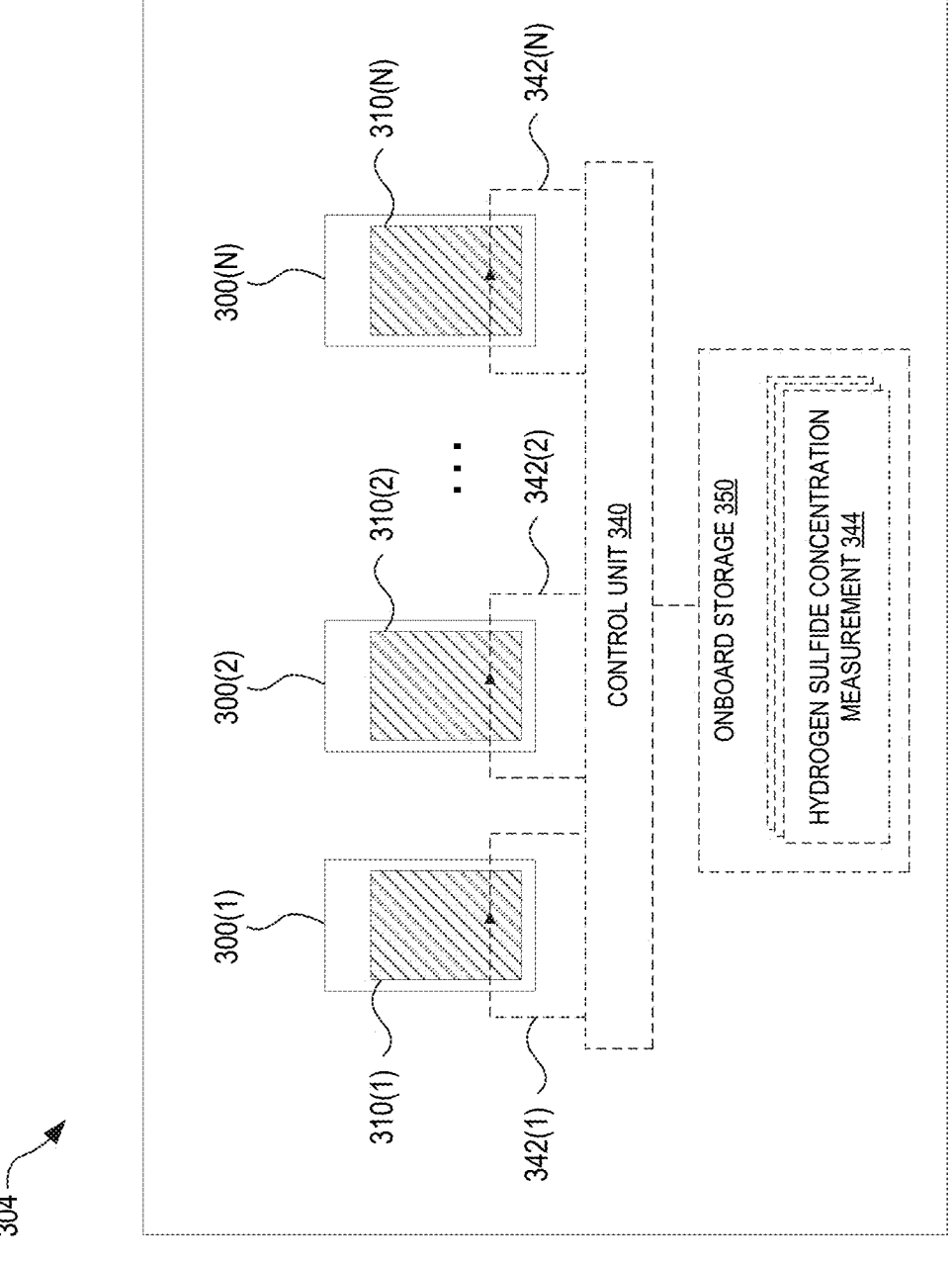
FIG. 3 illustrates a hydrogen sulfide sensing system that includes a plurality of sensors, each an example of the hydrogen sulfide sensor of FIGS. 1A, 1B, and 1C.

FIG. 3 illustrates a hydrogen sulfide sensing system 304 that includes a plurality of sensors 300, each an example of the hydrogen sulfide sensor 100 of FIGS. 1A, 1B, and 1C. The plurality of sensors 300 includes N sensors, labeled 300(1), 300(2), . . . 300(N) and each sensor 300 includes a homogeneous polyaniline sensing film 310 with electrical conductivity that depends on a concentration of hydrogen sulfide gas in contact with the sensor 300. The sensors 300 and homogeneous polyaniline sensing film 310 are respective examples of the hydrogen sulfide sensor 100 and homogeneous polyaniline sensing film 110 of FIGS. 1A, 1B, 1C and the descriptions of each respective elements apply between the two figures. In an embodiment, the electrical conductivity increases with increasing concentration of hydrogen sulfide and decreases with decreasing concentration of hydrogen sulfide, though other dependencies are included within the scope hereof.

In an embodiment, hydrogen sulfide sensing system 304 includes a control unit 340 that, for each sensor 300, induces an electrical current 342 to flow through the sensor 300 and generates a hydrogen sulfide concentration measurement 344 based at least in part on the electrical conductivity. In an embodiment, the hydrogen sulfide concentration measurements 344 may be stored in an onboard storage 350 communicatively coupled to the control unit 340. In an embodiment, each sensor 300 is configured to have a different detection threshold. In such an embodiment, hydrogen sulfide sensing system 304 includes a plurality of sensors 300 with a respective plurality of detection thresholds, such that each detection threshold corresponds to a different concentration of hydrogen sulfide (e.g., $\geq 1$ ppm, $\geq 10$ ppm, $\geq 25$ ppm, and $\geq 50$ ppm).

FIG. 4 is a flowchart illustrating a method 400 for detecting hydrogen sulfide. Method 400 may be used in conjunction with the hydrogen sulfide sensing system 304. Method 400 includes block 410, in which for each sensor of a plurality of sensors, a signal is generated if said sensor is exposed to a sample of hydrogen sulfide having gas density greater than or equal to a hydrogen sulfide detection threshold of said sensor, wherein the plurality of sensors has a respective plurality of hydrogen sulfide detection limits that span a detection range. In an embodiment, the method 400 includes that the detection range comprises two or more of 1 ppm, 10 ppm, 25 ppm, 50 ppm, 100 ppm, and 250 ppm hydrogen sulfide.

FIG. 5 is a flowchart illustration a method 500 for forming a hydrogen sulfide sensor. Method 500 may be used to form any of the hydrogen sulfide sensors 100, 200, and 300. Method 500 includes block 510, 520, and 530.

In block 510, method 500 includes depositing a pair of electrodes on a substrate. The pair of electrodes may be interdigitated electrodes. The electrodes may be chromium. The substrate may be glass. In an example of block 510, hydrogen sulfide sensor 100 includes a pair of interdigitated electrodes 120 deposited on substrate 130. In another example of block 510, a plotter coating system may be used to coat one of gold and silver on printed circuit board electrodes.

In block 520, method 500 includes dissolving a polyaniline polymer and a metal-chloride salt in an organic solvent to form a solution. The organic solvent may include dimethylformamide. The metal-chloride salt may include one or more of $CuCl_2$, $ZnCl_2$, and $FeCl_2$. In embodiments, the emeraldine base of polyaniline (PANI-EB) and metal chloride, such as $CuCl_2$, are dissolved in dimethylformamide to form a polymer solution. In the presence of a certain level of hydrogen sulfide, hydrogen sulfide may react with metal chloride to form a metal sulphide and release strong acid, HCl for example. The strong acid may then dope PANI-EB to form emeraldine salt (ES) and decrease the resistance of the polymer, making the polymer electrically conductive as illustrated in this example reaction:

$$CuCl2 + H_2S \rightarrow CuS(s) + 2HCl$$

$$PANI\text{-}EB + HCl \rightarrow PANI\text{-}H + (ES) + Cl-$$

Each species of metal in metal-chloride salt has a different efficiency for producing metal sulphide in the above reaction. As such, one or more types of metal chloride, such as $CuCl_2$, $ZnCl_2$, and $FeCl_2$, may be combined in varying concentrations to control reaction threshold and the derivative of electrical conductivity for detecting hydrogen sulfide. Accordingly, each hydrogen sulfide sensor can be configured to have one or both of a pre-determined detection threshold, at which the sensor becomes active, and a different derivative of electrical conductivity.

In block 530, method 500 includes spin-coating the solution to form a homogeneous sensing film disposed on the pair of electrodes. In an example of block 530, in hydrogen sulfide sensor 100, the homogeneous polyaniline sensing film 110 is formed by depositing a solution rather than by depositing a dispersion. Deposition of a solution leads to a homogeneous film while deposition of a dispersion leads to a patchy, inhomogeneous film. The homogeneous polyaniline sensing film 110 may for example be deposited using a spin-coating technique, though other solution-based deposition techniques may be used without departing from the scope hereof. In an embodiment, the homogeneous polyaniline sensing film has a thickness between 100 nanometers and 1 micron.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

Combinations of Features

Features described above as well as those claimed below may be combined in various ways without departing from the scope hereof. The following enumerated examples illustrate some possible, non-limiting combinations.

(A1) A hydrogen sulfide sensor includes a substrate, a pair of interdigitated electrodes disposed on the substrate, and a homogeneous polyaniline sensing film. The homogeneous polyaniline sensing film is disposed on the pair of interdigitated electrodes and has electrical conductivity that depends upon a concentration of hydrogen sulfide.

(A2) In embodiments of hydrogen sulfide sensor (A1), the homogeneous polyaniline sensing film becomes electrically conductive when the concentration of hydrogen sulfide is above a detection threshold.

(A3) In embodiments of hydrogen sulfide sensor (A2), the detection threshold is concentration of hydrogen sulfide selected from a group consisting of 1 ppm, 10 ppm, 25 ppm, 50 ppm, 100 ppm, and 250 ppm.

(A4) In embodiments of any of hydrogen sulfide sensors (A1)-(A3), the electrical conductivity increases with increasing concentration of hydrogen sulfide and decreases with decreasing concentration of hydrogen sulfide.

(A5) In embodiments of any of hydrogen sulfide sensors (A1)-(A4), the homogeneous polyaniline sensing film comprises a metal-chloride salt. A concentration of the metal-chloride salt is selected to achieve a conductivity derivative of the electrical conductivity with respect to concentration of hydrogen sulfide.

(A6) In embodiments of hydrogen sulfide sensor (A5), the metal-chloride salt includes one or more of $CuCl_2$, $ZnCl_2$, and $FeCl_2$. The metal-chloride salt is selected to achieve a rate-of-change of the electrical conductivity with respect to concentration of hydrogen sulfide.

(A7) In embodiments of hydrogen sulfide sensor (A5), the homogeneous polyaniline sensing film includes a polyaniline polymer, the concentration of which is selected to achieve a rate-of-change of the electrical conductivity with respect to concentration of hydrogen sulfide between 1 ppb and 250 ppm.

(A8) In embodiments of any of hydrogen sulfide sensors (A1)-(A7), the substrate includes glass.

(A9) In embodiments of any of hydrogen sulfide sensors (A1)-(A8), the pair of interdigitated electrodes includes chromium.

(A10) In embodiments of any of hydrogen sulfide sensors (A1)-(A9), the homogeneous polyaniline sensing film has a thickness between 100 nanometers and 1 micron.

(B1) A hydrogen sulfide sensing system includes a plurality of sensors, each with a homogeneous polyaniline sensing film having electrical conductivity that depends on a concentration of hydrogen sulfide.

(B2) In embodiments of system (B1), the electrical conductivity increases with increasing concentration of hydrogen sulfide and decreases with decreasing concentration of hydrogen sulfide.

(B3) Embodiments of any of systems (B1) and (B2), further includes a control unit that, for each sensor of the plurality of sensors, (i) induces an electric current to flow through said sensor, and (ii) generates a hydrogen sulfide concentration measurement based at least in part on the electrical conductivity.

(B4) In embodiments of any of systems (B1)-(B3), the plurality of sensors has a respective plurality of sensor rates corresponding to a detection range of hydrogen sulfide concentrations comprising two or more of 1 ppm, 10 ppm, 25 ppm, 50 ppm, 100 ppm, and 250 ppm.

(C1) A method for detecting hydrogen sulfide includes, for each sensor of a plurality of sensors, generating a signal if said sensor is exposed to a sample of hydrogen sulfide having gas density greater than or equal to a hydrogen sulfide detection threshold of said sensor. The plurality of sensors has a respective plurality of hydrogen sulfide detection limits that span a detection range.

(C2) In embodiments of method (C1), the detection range includes two or more of 1 ppm, 10 ppm, 25 ppm, 50 ppm, 100 ppm, and 250 ppm hydrogen sulfide.

(D1) A method for forming a hydrogen sulfide sensor includes (i) depositing a pair of electrodes on a substrate, (ii) dissolving a polyaniline polymer and a metal-chloride salt in an organic solvent to form a solution, and (iii) spin-coating the solution to form a homogeneous sensing film disposed on the pair of electrodes disposed on the substrate.

(D2) In embodiments of method (D1), in said step of depositing, the pair of electrodes being interdigitated electrodes.

(D3) In embodiments of any of methods (D1) and (D2), in said step of dissolving, the organic solvent is dimethylformamide.

(D4) In embodiments of any of methods (D1)-(D3), in said step of spin-coating, the pair of interdigitated electrodes includes chromium.

(D5) In embodiments of any of methods (D1)-(D4), in said step of dissolving, the metal-chloride salt includes one or more of $CuCl_2$, $ZnCl_2$, and $FeCl_2$.

(D6) In embodiments of any of methods (D1)-(D5), in said step of depositing, the pair of electrodes being chromium.

(D7) In embodiments of any of methods (D1)-(D6), in said step of depositing, the substrate being glass.

(D8) In embodiments of any of methods (D1)-(D5), said step of depositing includes coating printed circuit board electrodes with one of gold and silver.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A hydrogen sulfide sensor, comprising:

a substrate;

a pair of interdigitated electrodes disposed on the substrate; and a homogeneous polyaniline sensing film disposed directly on top of the pair of interdigitated electrodes and having electrical conductivity that varies with a concentration of hydrogen sulfide, wherein the homogeneous polyaniline sensing film comprises a metal-chloride salt.

2. The hydrogen sulfide sensor of claim 1, wherein the homogeneous polyaniline sensing film becomes electrically conductive when the concentration of hydrogen sulfide is above a detection threshold.

3. The hydrogen sulfide sensor of claim 2, wherein the detection threshold is concentration of hydrogen sulfide selected from a group consisting of 1 ppm, 10 ppm, 25 ppm, 50 ppm, 100 ppm, and 250 ppm.

4. The hydrogen sulfide sensor of claim 1, wherein the electrical conductivity increases with increasing concentration of hydrogen sulfide and decreases with decreasing concentration of hydrogen sulfide.

5. The hydrogen sulfide sensor of claim 1, wherein concentration of the metal-chloride salt is selected to achieve a conductivity derivative of the electrical conductivity with respect to concentration of hydrogen sulfide.

6. The hydrogen sulfide sensor of claim 5, wherein the metal-chloride salt comprises one or more of $CuCl_2$, $ZnCl_2$, and $FeCl_2$, the metal-chloride salt being selected to achieve a rate-of-change of the electrical conductivity with respect to concentration of hydrogen sulfide.

7. The hydrogen sulfide sensor of claim 1, wherein the homogeneous polyaniline sensing film comprises a polyaniline polymer, wherein concentration of the polyaniline polymer is selected to achieve a rate-of-change of the electrical conductivity with respect to concentration of hydrogen sulfide between 1 ppm and 250 ppm.

8. The hydrogen sulfide sensor of claim 1, wherein the substrate comprises glass.

9. The hydrogen sulfide sensor of claim 1, wherein the pair of interdigitated electrodes comprises chromium.

10. The hydrogen sulfide sensor of claim 1, wherein the homogeneous polyaniline sensing film has a thickness between 100 nanometers and 1 micron.

11. A method for detecting hydrogen sulfide using the hydrogen sulfide sensor of claim 1, comprising:

for each sensor of a plurality of sensors:

generating a signal if said sensor is exposed to a sample of hydrogen sulfide having gas density greater than or equal to a hydrogen sulfide detection threshold of said sensor;

wherein the plurality of sensors has a respective plurality of hydrogen sulfide detection limits that span a detection range.

12. The method of claim 11, wherein in said step of generating a signal, the hydrogen sulfide detection threshold is selected from the group consisting of 1 ppm, 10 ppm, 25 ppm, 50 ppm, 100 ppm, and 250 ppm hydrogen sulfide.

* * * * *